US008603006B2

(12) United States Patent
Mulqueeny et al.

(10) Patent No.: US 8,603,006 B2
(45) Date of Patent: Dec. 10, 2013

(54) METHOD AND APPARATUS FOR DETECTING INEFFECTIVE INSPIRATORY EFFORTS AND IMPROVING PATIENT-VENTILATOR INTERACTION

(75) Inventors: Qestra Camille Mulqueeny, Balmoral (AU); Stefano Nava, Pavia (IT)

(73) Assignee: ResMed Limited, Bella Vista (AT)

( * ) Notice: Subject to any disclaimer, the term of this patent is extended or adjusted under 35 U.S.C. 154(b) by 2006 days.

(21) Appl. No.: 11/664,730

(22) PCT Filed: Oct. 20, 2005

(86) PCT No.: PCT/AU2005/001627
§ 371 (c)(1),
(2), (4) Date: Apr. 5, 2007

(87) PCT Pub. No.: WO2006/079152
PCT Pub. Date: Aug. 3, 2006

(65) Prior Publication Data
US 2008/0110461 A1    May 15, 2008

Related U.S. Application Data

(60) Provisional application No. 60/619,957, filed on Oct. 20, 2004.

(51) Int. Cl.
*A61B 5/087* (2006.01)
*A61B 5/091* (2006.01)
*A61B 5/097* (2006.01)
*A61B 5/00* (2006.01)

(52) U.S. Cl.
USPC ....... 600/538; 128/204.23; 600/532; 600/533

(58) Field of Classification Search
None
See application file for complete search history.

(56) References Cited

U.S. PATENT DOCUMENTS

| | | | |
|---|---|---|---|
| 5,107,831 A | 4/1992 | Halpern et al. | |
| 6,015,388 A | 1/2000 | Sackner et al. | |
| 6,152,129 A | 11/2000 | Berthon-Jones | |
| 6,240,920 B1 | 6/2001 | Ström | |
| 6,305,374 B1 | 10/2001 | Zdrojkowski et al. | |
| 6,588,422 B1 | 7/2003 | Berthon-Jones et al. | |
| 6,626,175 B2 | 9/2003 | Jafari et al. | |
| 6,758,216 B1 | 7/2004 | Berthon-Jones et al. | |
| 2004/0050387 A1* | 3/2004 | Younes | 128/204.18 |

FOREIGN PATENT DOCUMENTS

| | | |
|---|---|---|
| EP | 0 956 877 | 11/1999 |
| JP | 2000-000307 | 1/2000 |
| WO | 2004/002561 | 1/2004 |
| WO | WO 2004/080516 A1 | 9/2004 |

OTHER PUBLICATIONS

Schuessler et al. An Adaptive Filter to Reduce Cardiogenic Oscillations on Esophageal Pressure Signals. Annals of Biomedical Engineering, 1998, vol. 26, pp. 260-267.*

(Continued)

*Primary Examiner* — Louise Humphrey
(74) *Attorney, Agent, or Firm* — Nixon & Vanderhye PC

(57) ABSTRACT

A method and system for detecting an ineffective effort of a patient being mechanically ventilated by a ventilator comprises (i) monitoring a respiratory flow of air of the patient after said ventilator has cycled; (ii) creating a signal indicative of said flow; (iii) removing artefact from said signal; (iv) monitoring said signal for perturbations; and (v) determining that an ineffective effort has occurred when said perturbation is significant.

30 Claims, 7 Drawing Sheets

(56) References Cited

OTHER PUBLICATIONS

Birch et al. An analogue instrument for the measurement of respiratory impedance using the forced oscillation technique. Physiological Measurement 2001, vol. 22, pp. 323-339.*

Stagmaier-stracca et al. Cough Detection using Fuzzy Classification. SAC 1995 Proceedings of the 1995 ACM symposium on Applied Computing. Association for Computing Machinery, New York, NY, USA © 1995, pp. 440-444.*

Japanese Office Action Mailed Feb. 8, 2011 for corresponding JP Appln. No. 2007-537070 and English translation, 13 pages.

International Search Report for PCT/AU2005/001627 mailed Dec. 15, 2005.

Tobin et al., *Patient-Ventilator Interaction*, American Journal of Respiratory and Critical Care Medicine, 163: 1059-1063, 2001.

Varon et al., *Prevalence of patient ventilator asynchrony in critically ill patients* [abstract], Chest. 106:141S, 1994.

Supplementary European Search Report for corresponding European Application No. 05856179, mailed May 25, 2010, 6 pages.

* cited by examiner

METHOD AND APPARATUS FOR DETECTING INEFFECTIVE INSPIRATORY EFFORTS AND IMPROVING PATIENT-VENTILATOR INTERACTION

CROSS-REFERENCES TO RELATED APPLICATIONS

This application is the US national phase of international application PCT/AU2005/001627 filed 20 Oct. 2005, which designated the U.S. and claims the benefit of U.S. Provisional Application No. 60/619,957, filed Oct. 20, 2004, each of which is incorporated herein by reference in its entirety.

BACKGROUND OF THE INVENTION

The invention relates to a method for the determination, and ultimately correction, of patient-ventilator asynchrony, e.g., asynchrony between ventilators that are assistive and are inclusive of patient triggered breaths, including but not limited to PSV, AC, AMV, and bilevel PS, and patients that can protect their airway and show some attempt to spontaneously breathe, including predominantly COPD, restrictive, mixed pathology and in general patients that require ventilatory assistance.

Problem Description

Patients with respiratory disorders or illness, and especially those with acute exacerbation, may have insufficient respiratory strength to maintain spontaneous breathing and require mechanical ventilatory assistance. The role and type of chosen ventilator is case specific, and varies in degree of respiratory participation, from Controlled Mechanical Ventilation (CMV) where the patient is completely passive, to forms of assisted ventilation which all share inspiratory effort with the patient after an active trigger of mechanical breath by the patient.

Forms of assisted ventilation vary by mode, e.g., parameter control (flow/volume/pressure), and amount of introduced assistance to the spontaneous breath, and include but are not limited to: assist control ventilation (AMV), synchronized intermittent mandatory ventilation (SIMV), and Pressure-Support Ventilation (PSV). Therapeutic efficacy is reliant upon synchrony between variable pressure/flow delivery and the patient's spontaneous respiratory cycle. Crucial to this is the ability of the ventilator to recognize when the patient initiates inspiratory effort (the trigger mechanism), and this is commonly achieved when the patient reaches either a positive flow threshold or minimal pressure threshold. In the case where patients fail to achieve this trigger threshold, patient-ventilator synchrony breaks down and may counteract any intended benefits otherwise seen using a ventilator. Otherwise known as ineffective triggering, this phenomenon has been observed in a variety of pathologies, however is most common in COPD. ("When receiving high levels of pressure support or assist control ventilation, a quarter to a third of a patient's inspiratory efforts may fail to trigger the machine." Tobin, et al. (Tobin M, Jubran A, Laghi F. Patient-Ventilator Interaction. American Journal of Respiratory and Critical Care Medicine. 163: 1059-1063, 2001.)).

A major cause of this asynchrony is expiratory flow limitation, dynamic hyperinflation of the lungs and concomitant intrinsic PEEP. Dynamic hyperinflation can result from either gas trapping behind closed airways, mismatching of mechanical vs. neural expiration, or a combination of the above. This has been well studied in COPD and to a lesser degree in other pathologies, however it has been observed in a variety of patients. The mechanisms follow: 1) Obstruction to the airway in COPD is caused by pathological effects such as airway secretions, bronchospasm, and mucosal edema. In all cases airflow resistance increases, and forces muscle recruitment to aid expiration resulting in dynamic compression of the airways. 2) In the case of emphysema also, respiratory system compliance may increase. The rate of lung emptying becomes impeded and the normal expiratory duty cycle time available (as determined by respiratory negative feedback control) is insufficient for complete mechanical expiration to occur. 3) In restrictive patients breathing occurs at low lung volumes and so promotes airway closure and gas trapping, especially if respiratory rate is high. In all cases, the end-expiratory lung volume (EELV) is not allowed to return to the elastic equilibrium volume of the respiratory system, and extraneous gas is trapped within the lung, namely dynamic hyperinflation.

The dynamic increase in EELV has several repercussions that inhibit inspiration in the spontaneously breathing patient:

Normally, the dynamic value of alveolar pressure, $P_{alv}$, that drives the direction of flow at any instant, remains positive during expiration and decays to zero elastic recoil pressure relative to the atmosphere at end-expiration, i.e., $P_{alv} = P_s e^{-t/RC}$, where $P_s$ is the static pressure plateau at end inspiration. In the presence of dynamic hyperinflation however, the equilibrium elastic recoil of the respiratory system is not achieved at end-expiration and $P_{alv}$ remains positive (intrinsic positive end-expiratory pressure or PEEPi). For inspiratory flow to start alveolar pressure must be negative relative to the atmosphere, so a patient's inspiratory muscles must first overcome this residual $P_{alv}$ or PEEPi before inspiratory flow occurs. In this context, PEEPi acts as an inspiratory load.

The dynamic increase in lung volume can also reduce the pressure generating capacity of the inspiratory muscles by shifting inspiratory muscle fibers from optimal length to shorter operational length and altering geometrical arrangements between diaphragm and chest wall.

The increase in volume may also result in the operation of the lung to be shifted higher into the non-linear, less compliant region of its volume-pressure curve at end-expiration. Due to the relative increased stiffness of the lung here, greater muscular effort to expand the lung and motivate inspiration is required.

In working against the above factors, the inspiratory muscles suffer fatigue and weakness that eventually lead to an inability to move air in and out of the lungs. Consequently, the patient achieves marginal flow or pressure change when efforts are made to inspire, and these inspiratory attempts may fail to achieve the trigger threshold and therefore go completely undetected by the ventilator.

FIG. 1 shows an example of a ventilator operating ideally in PSV mode (flow-triggered). Two full respiratory cycles are displayed. Flow and Pressure at the Airway Opening (PAO) are the signals available to the ventilator, and Pleural Pressure (PPL) is an external reference that indicates the onset of inspiratory patient effort by a negative deflection [1]. Approximately 300 ms after this event, the patient has achieved the requisite flow to trigger the ventilator [2] and IPAP is subsequently delivered [3].

In contrast, FIG. 2 illustrates the result of patient efforts that are undetected by the ventilator. Four inspiratory patient efforts are observed in the data series PPL, only the first of which has been supported by the ventilator as per the previous description [1]. The ensuing inspiratory efforts [2] have each brought about a respective rise in flow, however on each occasion the trigger threshold [3] was unachieved and consequently the ventilator has remained in EPAP.

Currently there are no existing automated metrics that identify and log occurrences of ineffective patient efforts during PV interaction. Varon et al. (Varon J, et al. Prevalence of patient ventilator asynchrony in critically ill patients [abstract]. Chest. 106:141S, 1994) identifies an "Asynchrony Index" as a percentage of monitored breaths that fail to trigger, however no further description of the means to obtaining this is provided. The authors note that the index varies with applied PEEP, that triggering asynchrony can be eliminated by reducing pressure support or tidal volume delivery in PSV and AC modes, respectively, and that the arousal state of patients proportionally affects the index, i.e., lower index during sleep than awake. These observations imply significant added value to the provision of a statistical reference to asynchrony in an assistive ventilator, and furthermore suggest that responsive action can resolve to mitigate asynchrony and minimize the work of breathing.

In the perfect patient-ventilator interaction, the ventilator would trigger in synchrony with electrical impulses originating in the central nervous system. While this may be virtually and ethically impossible to achieve in humans, detecting patient inspiratory efforts as close in time to this event is the ultimate goal to achieving synchronous patient-ventilator synchrony.

Further accounts suggest that triggering pressure support from pleural pressure improves PV synchrony, and the data in FIGS. 1 and 2 would support this theory. The measurement, however, is derived from balloon catheters inserted into the esophagus, and this level of invasiveness is undesirable and impossible for applications outside the ICU, e.g. home use.

Other methods for refined detection of patient effort in aid of improving ventilator triggering include using external sensors (U.S. Pat No. 6,758,216, U.S. Pat No. 6,015,388) and augmenting the triggering sensitivity algorithm internal to the ventilator (U.S. Pat. No. 6,626,175).

None of the above methods aims to address the major cause of ineffective efforts, namely the presence of dynamic hyperinflation and intrinsic PEEP in the patient's lungs.

A more meaningful solution is one that eliminates the effect of PEEPi and alleviates the regression of respiratory function at the outset. Commonly this is achieved with some success by adding external PEEP via the ventilator to offset PEEPi, such that at end-expiration, equilibrium exists between pressure at the mouth and that in the alveoli. Ultimately, it improves patient-ventilator interaction by reducing the magnitude of negative deflection in pleural pressure (brought about by inspiratory muscle effort) required to trigger the ventilator. PEEP also increases the functional residual capacity and respiratory compliance (at low volume) by recruiting previously collapsed, unventilated perfused airspaces, improving overall perfusion and $PaO_2$.

Thus, counterbalancing PEEPi with externally applied PEEP reduces the work of breathing and facilitates effective ventilator triggering. Determining the value of applied PEEP, however, presents difficulties for several reasons:

1) Too much will exacerbate dynamic hyperinflation (and associated problems), and may even cause barotrauma in certain patients. The ideal value has been shown to be highly dependent upon the existing level of PEEPi;

2) Static measurement of PEEPi is not possible without complete mechanical ventilation (passive participation of patient), and dynamic measurements are overestimated due to pressure contributions from both inspiratory and expiratory muscle groups;

3) even if absolute measurement was obtainable, PEEPi is highly variable from breath-to-breath and therefore a one-off measurement for external PEEP is not sufficient. Continuous PEEPi measurement and servo-regulated PEEP delivery would be optimal.

The first step toward addressing the first problem is deriving an appropriate ratio of PEEP to PEEPi to prevent further dynamic hyperinflation. It has been determined that added PEEP has little effect on the rate of lung emptying and therefore the level of dynamic hyperinflation, until it exceeds a critical value, $P_{crit}$. It remains to be seen with further investigation, however, what the precise relationship is, if any, between measured PEEPi and $P_{crit}$. As such, there is clinical argument as to what proportion $P_{crit}$ be of PEEPi in order to be effective but not detrimental (varies between 75% and 90%) and whether this should be relative to the dynamic or static value for PEEPi. Furthermore, a reliable and simple means for measuring PEEPi as a result of dynamic hyperinflation under dynamic conditions is yet to be developed. Thus, the clearest solution is contingent upon greater practical understanding and assessment of the problem than is current.

U.S. Pat. No. 6,588,422 describes a method and apparatus for counterbalancing PEEPi during ventilatory support of patients with respiratory failure. The invention attempts to deliver adjustable PEEP to the patient that offsets PEEPi dynamically. It addresses the problem of measuring PEEPi in real-time and non-invasively by analogy with measuring the degree of dynamic airway compression. Two main approaches are discussed for achieving this measurement: 1) by assignment to the ratio of inspiratory conductance and expiratory conductance using forced oscillation technique (FOT), and 2) examination of the shape of the expiratory airflow versus time curve.

Practically, however these solutions incur difficulties. Both techniques assume solid and idealized theoretical foundations that may be limited in practice. Furthermore, the FOT requirement of linearity necessitates the use of small amplitude oscillations, which may neglect other important nonlinear properties that manifest during tidal breathing. Also the methodological rigor required in the clinical setup, data collection and analysis, makes it less applicable to the unsupervised environment i.e. home ventilation.

Accordingly, a need has developed in the respiratory arts to develop a method by which one or more of the above deficiencies can be amended or eliminated.

BRIEF SUMMARY OF TH INVENTION

One aspect of the invention relates to an algorithm for the detection of missed triggers, and therefore unrecognized patient effort, during patient-ventilator (assisted) interaction. One function of the algorithm is to record when a significant perturbation on the flow signal occurs (indicative of patient effort) outside of the delivered inspiratory assistance (pressure support or volume controlled). The output of this algorithm is a time-referenced index of these events, which may serve as a statistical metric of patient-ventilator synchrony and therefore therapeutic success.

Another aspect, and perhaps the ultimate goal, is to minimize patient-ventilator asynchrony and reduce the work of breathing can be achieved accordingly by taking actions to minimize the index (either manually or servo-regulated)—by either altering ventilator parameters (increasing PEEP, decreasing Pressure Support, or reducing tidal volume delivery), and/or environmental factors (state of patient, drug administration).

Yet another aspect of the invention is to serve as a metric for the indexing of occurrences inspiratory patient efforts in patient-assistive ventilator interaction that have been undetected by the ventilator.

Another aspect of the invention is to provide an indication of true patient respiratory rate as the sum of ventilator delivered breaths and ineffective efforts detected.

Still another aspect of the invention is to minimize the occurrences of ineffective inspiratory patient efforts via servo-regulation of the ventilator, achieved by one or more of the following:

1) Servo-regulation of external PEEP delivery via the ventilator, using statistical reference to the metric, e.g., after a series of ineffective triggers, incrementally boost applied PEEP to minimize the index.
2) Servo-regulation of tidal volume delivery via the ventilator, using statistical reference to the metric, e.g., after a series of ineffective triggers, incrementally decrease tidal volume delivery to minimize the index.
3) Servo-regulation of pressure support delivery via the ventilator using statistical reference to the metric, e.g., after a series of ineffective triggers, incrementally reduce pressure support to minimize the index.
4) In flow-triggered ventilators, use of the algorithm to directly trigger IPAP, based on its impartiality to flow polarity, e.g., after a series of ineffective triggers, re-sensitize the trigger to minimize the index.

It is also an aspect of the invention to provide a reference for the clinician as to the patient's condition either in response to: 1) Disease progression and acute exacerbation and/or 2) Drug administration.

Statistics from the metric, e.g., occurrences or rate of missed triggers, can serve to: 1) Trigger an alarm indicating patient instability, 2) Act as a guide for appropriate patient management procedure, e.g., manual PEEP titration and/or 3) Log and track disease progression long term.

A further aspect of the invention is directed to a method for detecting and indexing inspiratory effort of COPD patients on assistive ventilators that have gone undetected and unsupported by the ventilators.

Another aspect of the invention is directed to a method servo-regulation of external PEEP delivery via the ventilator, using statistical reference to the metric, e.g. after a series of ineffective triggers, boost applied PEEP to minimize the index.

Still another aspect of the invention is directed to a method of sensitizing the ventilator flow trigger based on its impartiality to flow polarity. The algorithm can provide as an indicator to variable flow trigger thresholds, as required to minimize the index.

Further aspects of the invention may be directed to one or more of the following: a method for guidance of pharmacological administration; a metric of reference for manual adjustment of the applied PEEP by the clinician; an indicator of disease progression, to predict and alert of impending exacerbation; and/or a method of triggering an alarm for the clinician to adjust settings or manage a patient.

According to one embodiment of the invention, there is provided a method of detecting an ineffective effort of a patient being mechanically ventilated by a ventilator comprising the steps of (i) monitoring a respiratory flow of air of the patient after said ventilator has cycled; (ii) creating a signal indicative of said flow; (iii) removing artefact from said signal; (iv) monitoring said signal for perturbations; and (v) determining that an ineffective effort has occurred when said perturbation is significant.

According to another embodiment of the invention, there is provided a system for detecting an ineffective effort of a patient being mechanically ventilated by a ventilator comprising (i) means for monitoring a respiratory flow of air of the patient after said ventilator has cycled; (ii) means for creating a signal indicative of said flow; (iii) means for removing artefact from said signal; (iv) means for monitoring said signal for perturbations; and (v) means for determining that an ineffective effort has occurred when said perturbation is significant.

According to yet another embodiment of the invention, there is provided a system for detecting an ineffective effort of a patient being mechanically ventilated by a ventilator comprising a flow sensor to monitor a respiratory flow of air of the patient after said ventilator has cycled and to generate a signal indicative of said flow; and a processor to remove artefact from said signal, to monitor said signal for perturbations, and to determine that an ineffective effort has occurred when said perturbation is significant.

According to another aspect of the invention, perturbations in the flow signal that occur after the ventilator has cycled are classified according to a classification system. The classification system distinguishes ineffective efforts from other events such as coughs, swallows and signals of cardiogenic origin.

According to another aspect, monitoring ineffective efforts is used to measure compliance. In another form, the onset of exacerbations of the patient's condition is detected using a measure of ineffective efforts.

In another form, Positive End Expiratory Pressure (PEEP) is adjusted in accordance with a measure of ineffective efforts. In another form, pressure support is adjusted in accordance with a measure of ineffective efforts. In another form tidal volume and/or flow delivery is adjusted in accordance with a measure of ineffective efforts.

According to still another aspect of the invention, there is provided a ventilator system for a patient, comprising a blower to produce a source of pressurized breathable gas; and a patient interface (e.g., mask, cannulae, prongs, puffs, etc.) to deliver the breathable gas to the patient's airways. The ventilator system includes a processor (e.g., a general purpose computer or the like), program, algorithm, hardware and/or software configured to carry out any of the methods described herein. For example, the ventilator is at least partially controlled based on a measure of breathing effort of the patient as determined by the processor.

These and other aspects will be described in or apparent from the following detailed description of preferred embodiments.

DETAILED DESCRIPTION OF PREFERRED EMBODIMENTS

While the following embodiments may be explained in terms of a sequential process, it is understood that the process can be carried out using a non-linear, non-sequential, or non-staged process, or the order of the process may be changed. Also while the following describes an entire process, aspects of the invention may relate to only a subset of that process.

One aspect of the invention is directed to a method for improving patient-ventilator synchrony, and eliminates the need for external sensors, measuring intrinsic PEEP (or by analogy), or modifying/complicating the triggering sensitivity algorithm internal to the ventilator. Rather, it identifies unsupported patient effort exhibited as a specific feature in the flow or pressure signal, indexes their occurrences, and optionally uses the output as an error function that is forced to minimize over time by adjusting various ventilator/environmental parameters. These adjustments are either manual or servo-regulated, and may involve PEEP and/or tidal volume delivery (to counterbalance PEEP and reduce dynamic hyperinflation), as well as trigger sensitivity.

In one embodiment, an algorithm is provided for detecting missed triggers corresponding to patient effort without the benefit of a direct effort sensor. Only patient flow and airway pressure signals are processed to determine this.

Figure 1:
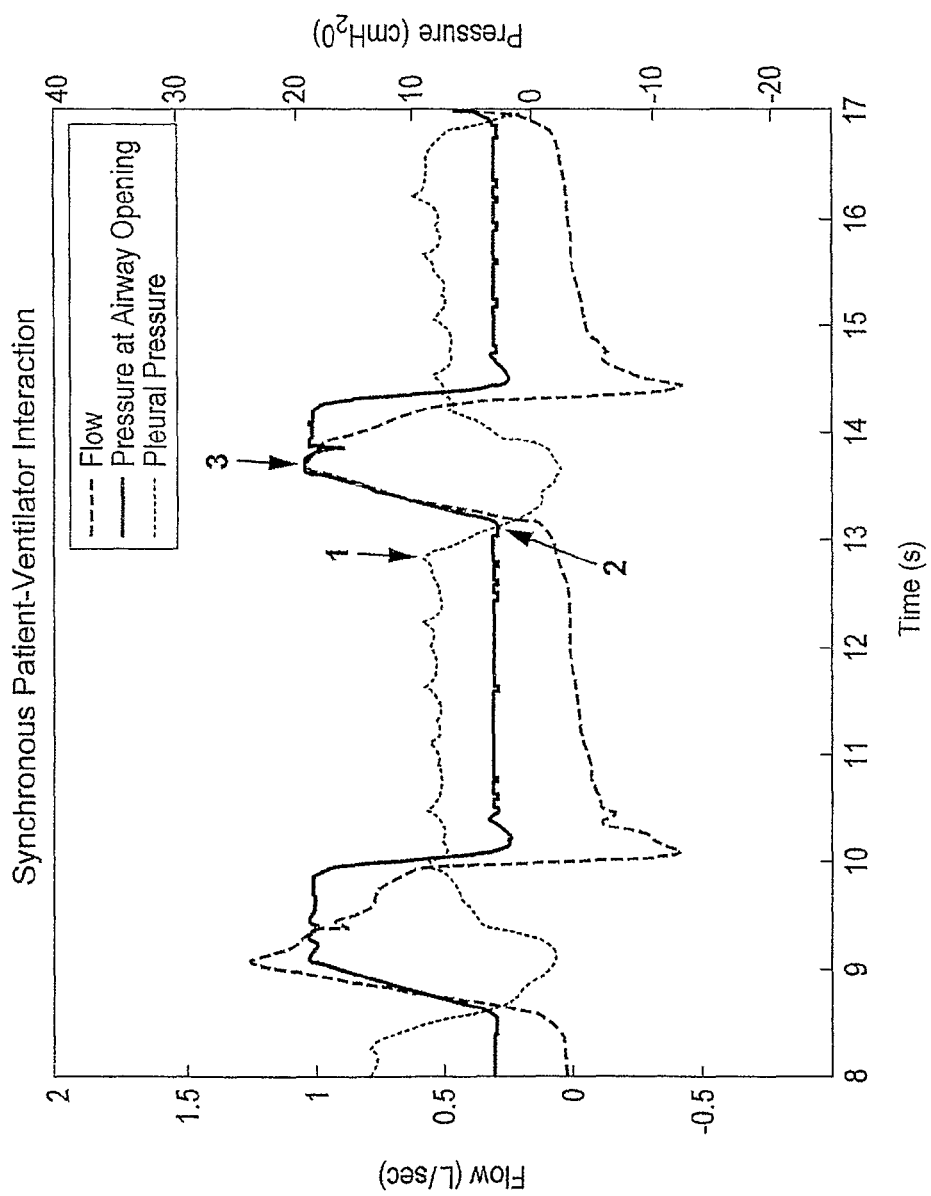
FIG. 1 is a graph illustrating an example of synchronous patient-ventilator interaction in PSV mode.
Figure 2:
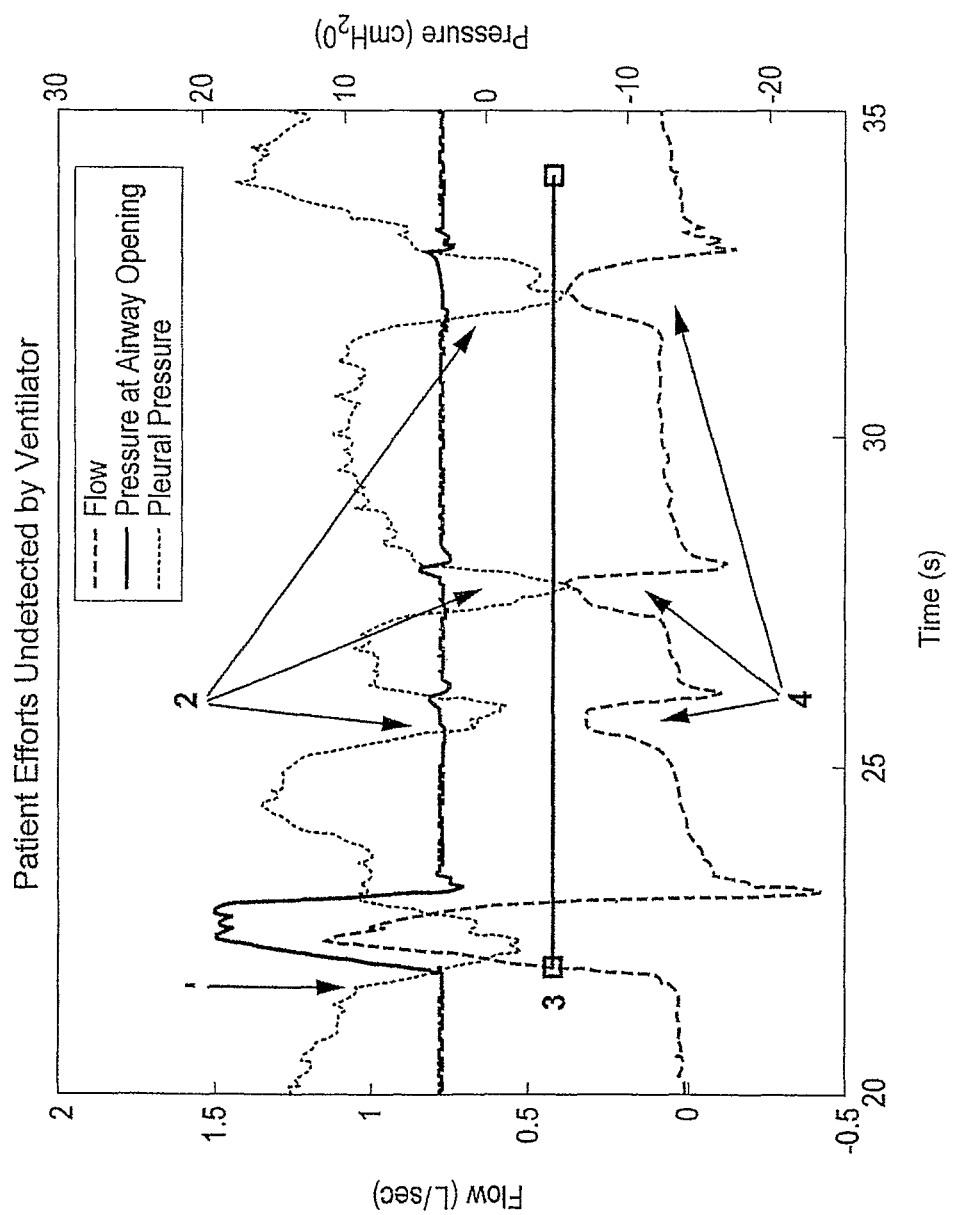
FIG. 2 is a graph illustrating asynchronous patient-ventilator interaction.

As shown in FIG. 2, unsupported efforts accompany significant and unique perturbations in the flow signal [4] and this is a common phenomenon. These perturbations:
- occur during expiration after the ventilator cycles and before it next triggers, i.e. in the absence of successful inspiratory assistance;
- are not necessarily characterized by positive-directional flow, but rather by retarded negative flow.
- are 'significant' in that they are distinguishable from noise or other low amplitude phenomena such as secretions, or cardiogenic oscillation, etc.
- are 'unique' in that they may be distinguishable from significant perturbations caused by other physiological phenomena such as swallowing or cough.

Figure 3:
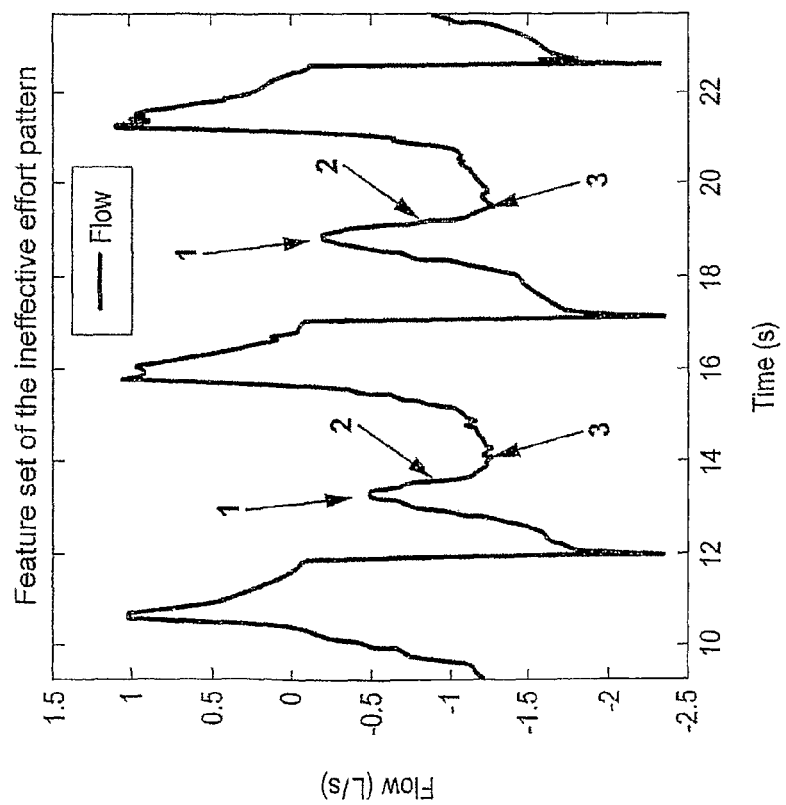
FIG. 3 is a graph illustrating the feature set of a single ineffective effort pattern.

Several features on the flow signal can be identified as characteristic of an individual ineffective effort, shown in FIG. 3. Together in sequence they form a feature set. During uninterrupted expiration, and after achieving the peak expiratory flow, the flow profile accelerates towards zero. This trend may be exponential for normal subjects, or approaching a linear decay for expiratory flow limited subjects. When an ineffective effort occurs on the expiratory curve there may or may not be a short, rapid (relative to the expiratory baseline) deceleration in negative flow corresponding to the onset in muscle effort, but always a local maximum [1] and a short, fairly rapid declivity [2] back to the baseline of the expiratory flow profile punctuated with a local minimum [3].

Figure 4:
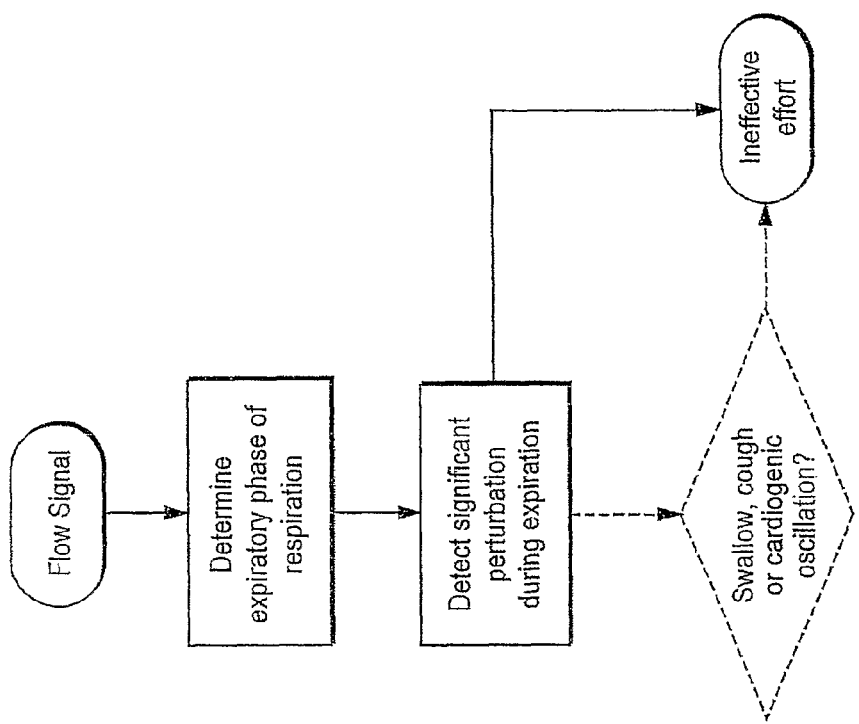
FIG. 4 is a schematic flow chart summarizing a high-level approach for monitoring of asynchrony according to embodiments of the present invention.

One aspect of the invention relates to the identification of expiration on the flow signal, as well as significant and unique perturbations on this portion of the signal pertaining to ineffective efforts. This involves identification of at least the local maximum, and furthermore the declivity in succession. In addition, an aspect of the invention encapsulates a general classifier of perturbations on the flow signal during expiration relating them to their physiological cause, including swallowing, coughing and cardiogenic oscillation, such that ineffective efforts can be uniquely distinguished with greater confidence. Refer to FIG. 4 for a high-level flow chart description.

One embodiment of the invention that detects ineffective efforts as significant local maxima occurring during expiration may be implemented as follows. A flow chart of the process is included in FIG. 5.

Preliminary signals processing comprises the following steps:
1) Two signals are recorded from a ventilated patient using a logging device including a data-acquisition system and memory, which may be the ventilator itself. These signals are airflow (Q) and airway pressure at the mouth (P).
2) The flow and airway pressure signals are passed through a smoothing/noise filter to minimize noise. One such example is a Butterworth low pass filter with low order to minimize phase lag and a cut-off frequency of 1 Hz.
3) An unintentional leak compensation algorithm is applied to the flow signal such as that described in U.S. Pat. No. 6,152,129 (Berthon-Jones).
4) The first derivative (Q') of the flow signal is calculated.
5) The second derivative (Q") of the flow signal is calculated.

Figure 6C:
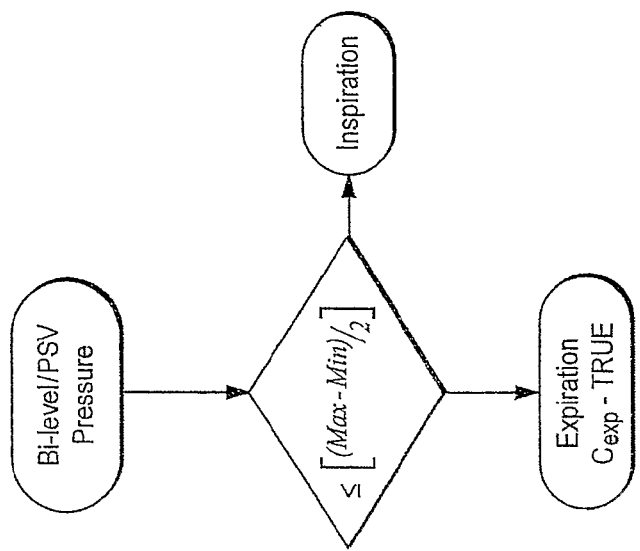
FIG. 6a-6c are schematic flow charts for the identification of the expiratory phase of respiration.
Figure 6B:
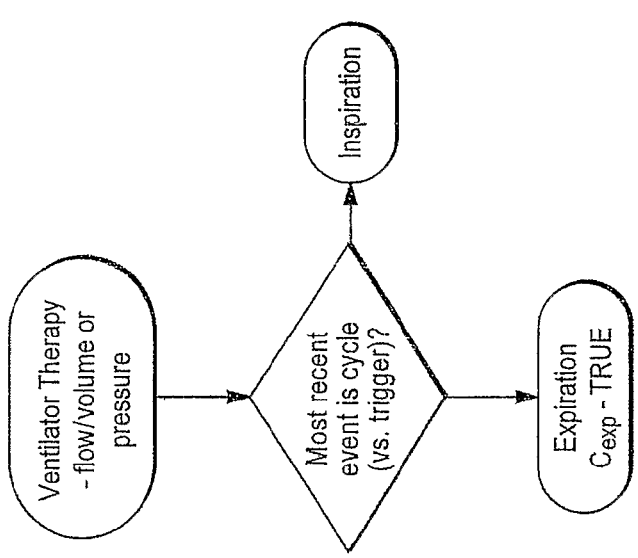
Figure 6A:
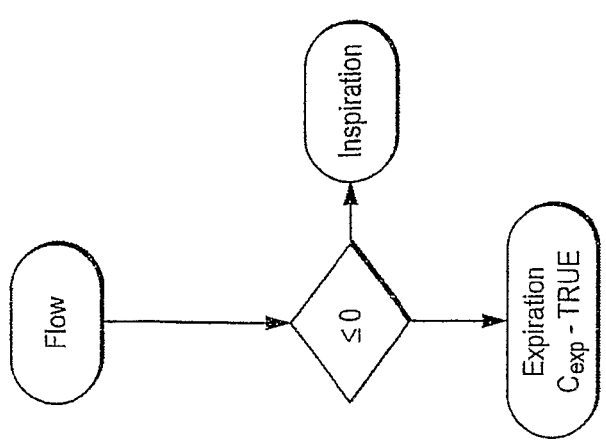
Figure 7:
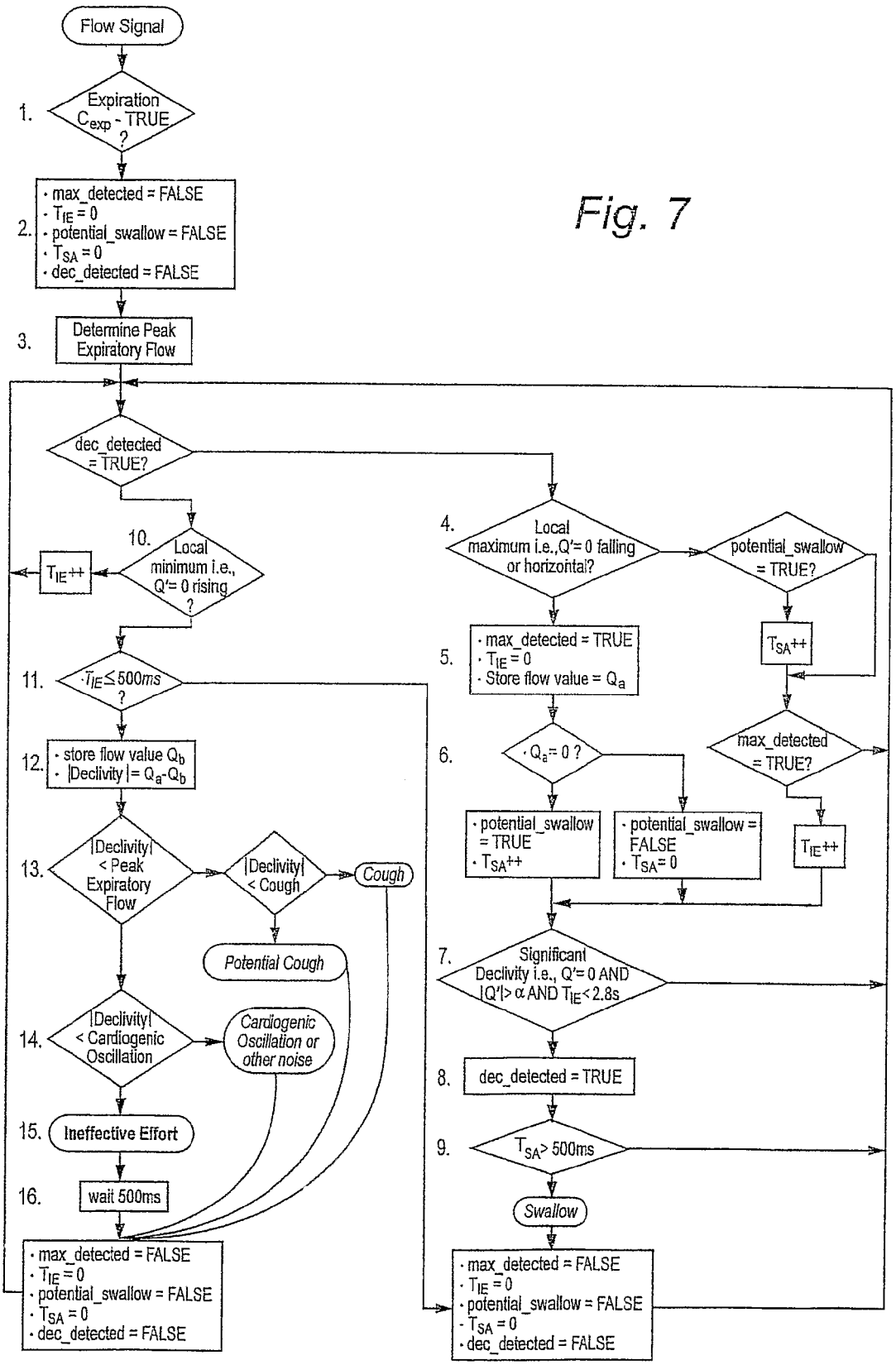
FIG. 7 is a schematic flow chart for monitoring of asynchrony according to one embodiment of the present invention.

Three Boolean control signals are derived from the preprocessed signals:
1) An indicator of expiratory phase. This can be achieved using any number of means for example classifying respiratory phase based on the polarity of the flow (FIG. 6(*a*)) or alternatively based on determining the state of therapy delivery using the trigger and cycle events (FIG. 6(*b*)), or testing the pressure signal against a phase transition threshold (FIG. 6(*c*)) (e.g. ((IPAP or maximum pressure)−(EPAP or minimum pressure))*50%, depending upon type of assistance). The resultant control signal, $C_{exp}$, may be TRUE during expiration.
2) An index that indicates the zero-crossings in the first derivative flow signal. The resultant control signal, $C_{Q'}$ is TRUE when Q'=0, and identifies inflections in the flow signal.
3) A control signal that ensures a) the inflections identified by step 2 are maxima; and b) the inflections have significant rise to qualify as a feature, distinguished from noise or cardiogenic flow. This may be achieved by testing the second derivative flow signal against an impartial negative, non-zero threshold α, for example, but not limited to, its own standard deviation or percentage thereof, defined as:

$$STD(F) = \sqrt{\frac{1}{n-1}\sum_{i=1}^{n}(F_i - \overline{F})^2}, \text{ where } \overline{F} = \frac{1}{n}\sum_{i=1}^{n}F_i$$

The resultant control signal, $C_{Q''}$, is TRUE when less than −α.

The above control signals are logically AND-ed to derive the resultant index where INDEX=TRUE for every detected ineffective effort.

Another embodiment of the invention detects ineffective efforts as a feature set occurring during expiration and comprising a significant local maximum and successive declivity, that also has parameters unique to its physiological cause. It may be implemented as follows.

Preliminary signals processing comprises the following steps:
1) Two signals are recorded from a ventilated patient using a logging device including a data-acquisition system and memory, which may be the ventilator itself. These signals are airflow (Q) and airway pressure at the mouth (P).

2) The flow and airway pressure signals are passed through a smoothing/noise filter to minimize noise. One such example is a Butterworth low pass filter with low order to minimize phase lag and a cut-off frequency of 1 Hz.
3) An unintentional leak compensation algorithm is applied to the flow signal such as that described in U.S. Pat. No. 6,152,129 (Berthon-Jones).
4) The first derivative (Q') of the flow signal is calculated.
5) The second derivative (Q") of the flow signal is calculated.

An indicator of expiratory phase is determined. This can be achieved using any number of means for example classifying respiratory phase based on the polarity of the flow (FIG. 6(a)) or alternatively based on determining the state of therapy delivery using the trigger and cycle events (FIG. 6(b)), or testing the pressure signal against a phase transition threshold (FIG. 6(c)) (e.g. ((IPAP or maximum pressure)−(EPAP or minimum pressure))*50%, depending upon type of assistance). The resultant control signal, $C_{exp}$, may be TRUE during expiration.

Figure 5:
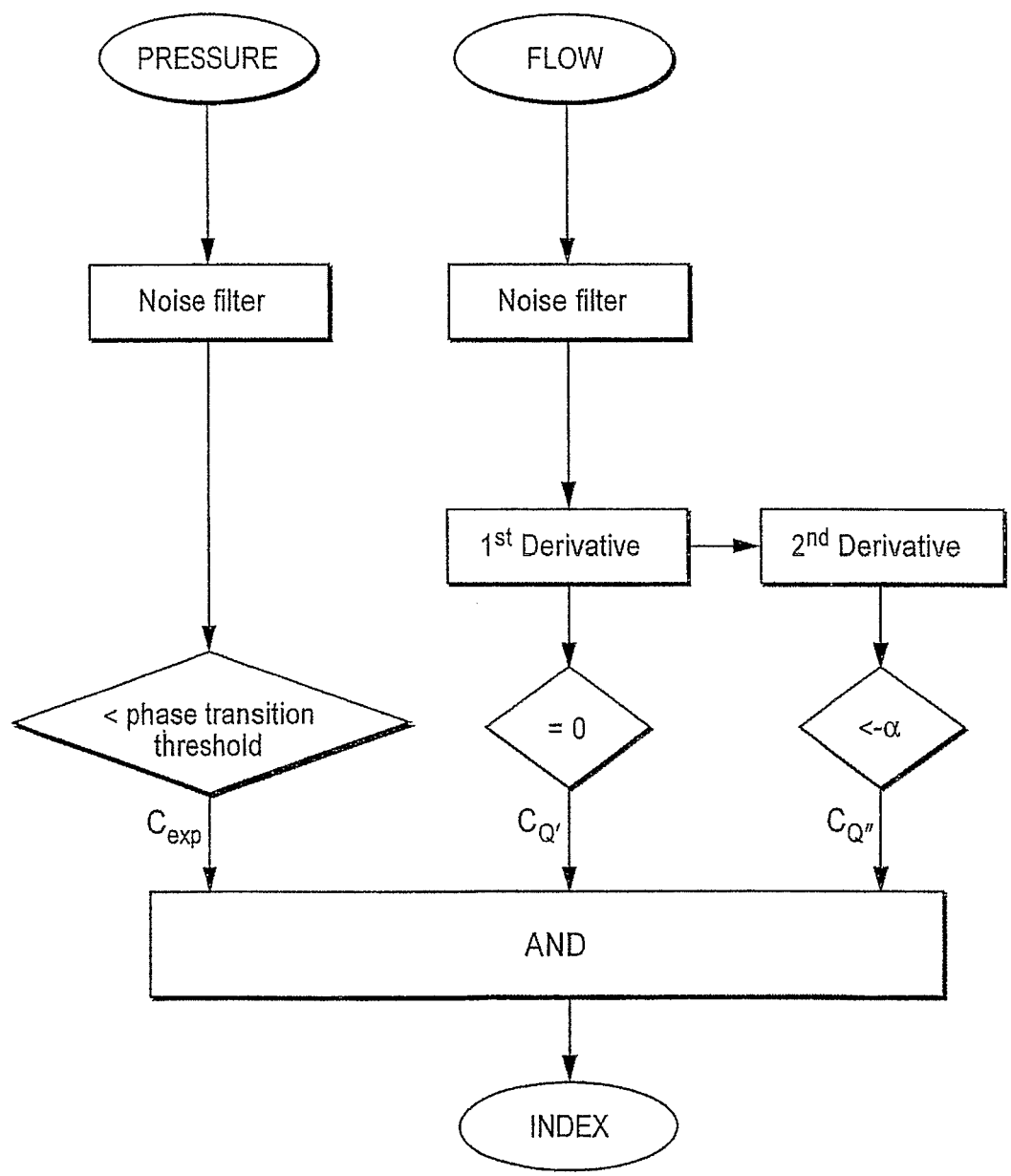
FIG. 5 is a schematic flow chart for monitoring of asynchrony according to one embodiment of the present invention.

The combined perturbation feature set detection and pattern classifier is described by the following and shown in the flow chart of FIG. 5. Features referred to have been described and are illustrated in FIG. 3.

The expiratory phase control signal is checked for TRUE to indicate whether to process the flow for perturbation detection [1].

The following state variables and timers are initialized [2]:
1. max_detected—indicates whether a local maximum has occurred
2. $T_{IE}$—elapsed time since onset of most recent local maximum i.e. onset of patient effort decay
3. potential_swallow—indicates whether the patient may be swallowing
4. $T_{SA}$—elapsed time since the onset of a potential swallow
5. dec_detected—indicates whether a significant declivity has yet been detected.

Peak expiratory flow (PEF) occurs early in uninterrupted expiration and is calculated prior to perturbation detection [3] by:

$$\text{if } (Q_i > Q_{i-1}), \text{ then PEF} = Q_i$$

where i indicates the sample sequence. In the case that PEF exceeds a threshold of approximately 200 Lmin$^{-1}$, a cough is considered to have occurred and PEF is assigned a null value.

Detection of the local maximum feature is given priority [4], and is determined by the occurrence of either a falling zero-crossing or exactly zero slope on the first derivative:

$$Q'_i < 0 \text{ and } Q'_{i-1} > 0, \text{ or } Q'_i = 0$$

Upon detection of a local maximum, the max_detected state variable is asserted and $T_{IE}$ reset. The value of flow at the local maximum is stored as the variable $Q_a$ [5].

$Q_a$ is tested for near-zero value to identify a possible swallow event [6]. A swallow occurring in mid-expiration may be a perturbation with a similar feature set as an ineffective effort. It may be distinguished however as a temporary occlusion of the airway and hence period of apnea or zero flow. The expected duration of swallowing apnea is considered to be at least 500 ms. If this test proves true the state variable potential_swallow is asserted and the swallow apnea timer $T_{SA}$ is incremented by the sample time.

Until a significant declivity is detected, incoming flow samples are processed in this set of loops, that firstly identify a local maximum and start an ineffective effort timer, and secondly identify the potential for a swallow to be occurring and if so, start a swallow apnea timer. Both timers are incremented each iteration by an amount equal to the sample time.

A significant declivity is identified [7] by the occurrence of a maximum in the rate of change of decreasing flow (Q"=0) such that its value is greater than an impartial negative, non-zero threshold a, for example but not limited to, a percentage (e.g. 33%) of the standard deviation, defined as:

$$STD(F) = \sqrt{\frac{1}{n-1}\sum_{i=1}^{n}(F_i - \overline{F})^2}, \text{ where } \overline{F} = \frac{1}{n}\sum_{i=1}^{n}F_i$$

and n is the number of samples in a long window or circular buffer that progressively shifts with incoming flow.

To indicate detection of this significant declivity feature, the state variable dec_detected is asserted [8].

To classify whether or not the declivity is the result of a swallow, the swallow apnea timer is checked if greater than the minimum expected swallow period, 500 ms [9], and if so, the feature detection process is reset including all state variables and timers.

If a declivity has been detected that is not the result of a swallow, the next local minimum is ascertained by the occurrence of a rising zero-crossing on the first derivative:

$$Q'_i > 0 \text{ and } Q'_{i-1} < 0$$

Upon detection of this local minimum, the total duration of the declivity and thus the decay in patient effort is given by the timer value $T_{IE}$. For values greater than 500 ms the feature set is considered unfeasible as an ineffective effort and is disregarded [11].

The value of flow at the local maximum is stored as the variable $Q_b$ and the amplitude of the declivity is defined [12] as:

$$|\text{Declivity}| = Q_a - Q_b$$

The amplitude of the declivity is used to classify the feature set in terms of its physiological cause. Other than ineffective efforts, the most common physiological explanations of significant perturbations, and more precisely declivities, that occur during expiration, are secretions, coughs and cardiogenic oscillations (CGO).

Secretions in the patient may be observed on a high-resolution flow signal as high frequency crackle shortly after the onset of expiration. Down-sampling or noise filtering the signal may eliminate the presence of this crackle, without eliminating the higher frequency components of the ineffective effort. In accordance with the filtering techniques in the present embodiments, secretions have little or no effect.

A cough is a sudden, spasmodic contraction of the thoracic cavity, resulting in violent release of air from the lungs. In mid-expiration, the flow achieved can be greater than 200 L/min, extending well beyond the peak expiratory flow. These thresholds are used to test the amplitude of the declivity [13].

In obstructive patients with high resistance and low lung compliance, CGO are not well propagated, if at all, to the mouth. Their presence may be damped by down-sampling or noise-filtering, or suppressed using techniques such as adaptive filtering using a cardiac-gated signal such as an ECG or pulse plethysmograph.

In cases where CGO is present on the flow signal and has not been suppressed, it is possible to distinguish them from ineffective efforts, based on their smaller peak-trough or declivity amplitude. A threshold of 4 L/min is used in this embodiment [14].

If the amplitude of the declivity is within the overall constraints, an ineffective effort is said to have occurred.

A wait period is imposed after the detection of an ineffective effort and before the detection of a new local maximum that corresponds to a successive ineffective effort [16]. This is based on the expectation that the minimum neural time, and hence effort, for attempted inspiration is 500 ms.

Figure 8:
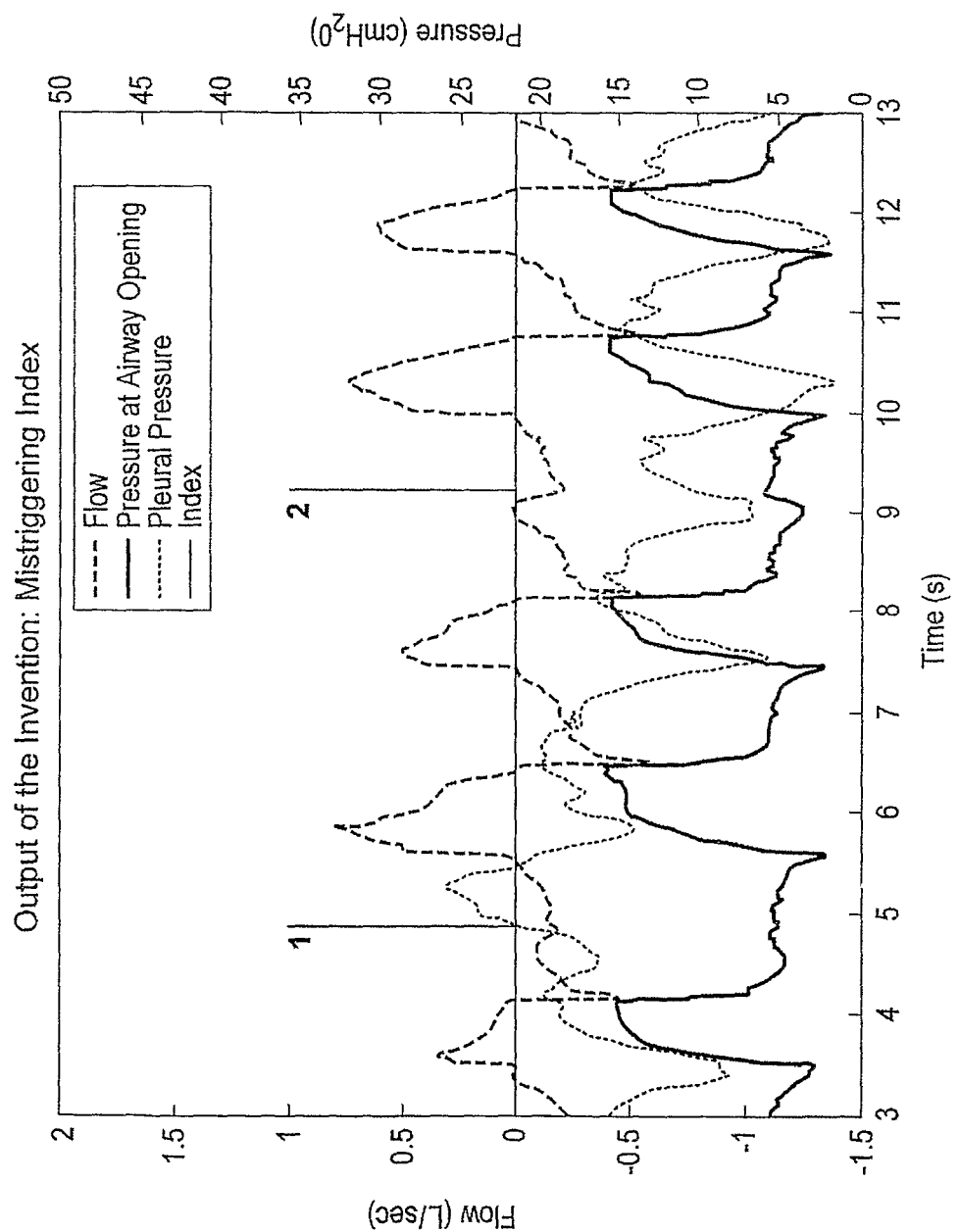
FIG. 8 is a graph illustrating operational results achieved using an embodiment of the present invention.

The output of an embodiment of the invention is shown in FIG. 8. Two unsupported inspiratory efforts matched with significant perturbations in the flow signal are evident, [1] and [2], and these have been recognized and logged by the algorithm shortly afterwards in time.

These embodiments are exemplary of the feasibility of the invention, and such descriptions are not to be taken as limitations.

Another aspect of the invention relates to using an index of ineffective efforts to estimate true patient respiratory rate. In one form this is done by summing the number of ineffective efforts detected as described above together with the number of ventilator delivered breaths in a time period.

Another aspect of the invention relates to improving patient-ventilator asynchrony. A cumulative sum of the algorithm output over periodic intervals or for a set number of respiratory cycles (an index statistic) can be used as an indicator of therapeutic efficacy. In the case of high missed triggers as a result of the patient's condition (high PEEPi, acute exacerbation), or incorrect ventilator settings, the metric can facilitate an alarm for the clinician to take responsive action (drug administration or PEEP/Pressure Support/tidal volume delivery adjustment), and also measure the effectiveness of that action with reference to the index statistic prior to it.

Extending this concept, responsive action to the index statistic i.e. adjustment of ventilator settings PEEP/Pressure Support/tidal volume delivery may be automated in the ventilator itself. Furthermore, continuous assessment of the efficacy of these adjustments and thus servo-regulation of therapy would be enabled.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

For example, instead of a flow signal being monitored, a pressure signal is monitored at the entrance to the patient's airways. One form of feature set applicable for a pressure signal is inversely related to the feature set described above in relation to flow. For example, instead of a declivity being detected, the pressure signal is monitored for a sharp increase following a local minimum.

In addition, while the invention has particular application to patients who suffer from COPD, it is to be appreciated that patients who suffer from other illnesses (e.g., congestive heart failure, diabetes, morbid obesity, stroke, barriatric surgery, etc.) can derive benefit from the above teachings.

The invention claimed is:

1. A system for detecting an ineffective effort of a patient being mechanically ventilated by a ventilator, the system comprising:
    a flow sensor that is configured to:
        monitor a respiratory flow of air of the patient during expiration that is after cycling of the ventilator and before triggering of the ventilator; and
        generate a signal indicative of the respiratory flow of the patient during expiration;
    a processing system that includes at least one processor, the processing system configured to:
        determine a peak expiratory flow (PEF) of the patient based on the generated signal;
        calculate a second derivative of the signal that is indicative of the respiratory flow of the patient during expiration;
        determine an occurrence of a significant declivity within the signal when the second derivative of the signal is greater than a negative, non-zero threshold; and
        detect perturbations within the generated signal by classifying the perturbations between at least ineffective efforts and non-ineffective efforts based on determination of the occurrence of the significant declivity within the signal.

2. A system as claimed in claim 1, wherein said non-ineffective efforts include at least one of a signal representative of: cardiogenic oscillation, a cough, secretions, and/or a swallow.

3. A system as claimed in claim 1, further comprising a noise filter that is configured to remove non-ineffective efforts from the generated signal.

4. A system as claimed in claim 1, wherein the processing system is further configured to detect perturbations by detecting a local maximum within the generated signal.

5. A system as claimed in claim 2, wherein the processing system is further configured to determine an elapsed time period since the onset of a potential swallow.

6. The system of claim 1, wherein the processing system is further configured to determine that a cough has occurred when the PEF exceeds a threshold.

7. The system of claim 6, whereby said threshold is approximately 200 L per minute.

8. The system of claim 4, wherein the processing system is further configured to determine a flow value that occurs at said local maximum.

9. The system of claim 8, wherein the processing system is further configured to determine that a potential swallow has occurred when the flow value is near zero.

10. The system of claim 9, wherein the processing system is further configured to start a swallow timer when the flow value at said local maximum is near zero.

11. The system of claim 10, wherein the processing system is further configured to determine that a swallow has occurred when said swallow timer is greater than about 500 ms.

12. The system of claim 1, wherein the processing system is further configured to calculate a standard deviation based on the generated signal, wherein the negative threshold is a percentage of the standard deviation.

13. The system of claim 12 whereby said percentage is approximately 33%.

14. The system of claim 2, wherein the processing system is further configured to modify the generated signal by removing a signal representative of cardiogenic oscillation by down-sampling or noise-filtering.

15. The system of claim 2, wherein the processing system is further configured to modify the generated signal by removing a signal representative of cardiogenic oscillation by distinguishing cardiogenic oscillations on the basis of amplitude.

16. The system of claim 15 whereby cardiogenic signals have an amplitude of less than approximately 4 L per minute.

17. The system of claim 1, wherein the processing system is further configured to determine an end of the significant declivity by detecting a local minimum.

18. The system of claim 17, wherein the processing system is further configured to determine an amplitude of the significant declivity.

19. The system of claim 18, wherein determination of the amplitude of the significant declivity includes subtracting a flow value at said local minimum from a flow value at a local maximum.

20. The system as claimed in claim 18, wherein the processing system is further configured to determine that a cough has occurred when the amplitude of the significant declivity is greater than a threshold.

21. The system of claim 20 whereby said threshold is the PEF.

22. The system of claim 20 whereby said threshold is approximately 200 L/min.

23. A ventilator system for a patient, comprising:
   a blower to produce a source of pressurized breathable gas;
   a patient interface to deliver the breathable gas to the patient's airways; and
   a system according to claim 1,
   wherein the ventilator system controls the delivery of breathable gas from the blower based on a breathing effort measurement that is determined in accordance with the processing system.

24. A system as claimed in claim 23 wherein a Positive End Expiratory Pressure (PEEP) is adjusted based on the breathing effort measurement.

25. A system as claimed in claim 24 wherein when the patient has COPD said adjustment of PEEP is limited to 6 cm H2O.

26. A system as claimed in claim 24, further comprising a sensor that is configured to measure oxygen saturation of the patient.

27. A system as claimed in claim 26, wherein adjustment of PEEP is a function of the measured oxygen saturation.

28. A method of determining a measure of patient compliance with a mechanical ventilator, the method comprising:
   detecting ineffective efforts with the system of claim 24;
   recording, onto a storage medium, a signal that is indicative of the said ineffective efforts over time;
   calculating a parameter based on the stored signal;
   determining a measure of patient compliance based on the calculated parameter.

29. A method of detecting the onset of exacerbations of a patient that is mechanically ventilated, the method comprising:
   detecting ineffective efforts of a patient with the system of claim 24;
   determining a rate at which the ineffective efforts occur; and
   determining that an onset of exacerbations have occurred when said rate changes.

30. A method of detecting the respiratory rate of a mechanically ventilated patient, the method comprising:
   detecting the presence of ineffective efforts based on the system of claim 24;
   monitoring a rate at which said ineffective efforts occur;
   monitoring a rate of ventilator assisted breaths; and
   determining a respiratory rate of the patient from a sum of the rate of ineffective efforts and the rate of ventilator assisted breaths.

* * * * *

UNITED STATES PATENT AND TRADEMARK OFFICE
CERTIFICATE OF CORRECTION

PATENT NO. : 8,603,006 B2  Page 1 of 1
APPLICATION NO. : 11/664730
DATED : December 10, 2013
INVENTOR(S) : Mulqueeny et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1983 days.

Signed and Sealed this
Twenty-second Day of September, 2015

Michelle K. Lee
*Director of the United States Patent and Trademark Office*